US011003908B2

(12) United States Patent
Koch et al.

(10) Patent No.: US 11,003,908 B2
(45) Date of Patent: May 11, 2021

(54) REMOTE-SENSING-BASED DETECTION OF SOYBEAN APHID INDUCED STRESS IN SOYBEAN

(71) Applicant: Regents of the University of Minnesota, Minneapolis, MN (US)

(72) Inventors: Robert L. Koch, Minneapolis, MN (US); Ian V. MacRae, Minneapolis, MN (US); Zachary Peter Dragan Marston, Minneapolis, MN (US); David Mulla, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 65 days.

(21) Appl. No.: 16/519,233

(22) Filed: Jul. 23, 2019

(65) Prior Publication Data
US 2021/0027056 A1    Jan. 28, 2021

(51) Int. Cl.
*G06K 9/00* (2006.01)
*A01H 5/00* (2018.01)
*G06K 9/62* (2006.01)
*G06K 9/46* (2006.01)
*G06T 7/70* (2017.01)
*G01N 21/3563* (2014.01)
(Continued)

(52) U.S. Cl.
CPC ....... *G06K 9/00657* (2013.01); *G01N 21/359* (2013.01); *G01N 21/3563* (2013.01); *G01N 33/025* (2013.01); *G06K 9/4661* (2013.01); *G06K 9/6256* (2013.01); *G06K 9/6262* (2013.01); *G06K 9/6267* (2013.01); *G06T 7/70* (2017.01); *G06T 2207/30242* (2013.01)

(58) Field of Classification Search
USPC ............... 382/100, 103, 108–110, 156, 162, 382/172–173, 181, 191, 199, 209, 219, 382/224, 232, 254, 274, 276, 286, 305; 1/1; 800/298, 260
See application file for complete search history.

(56) References Cited

U.S. PATENT DOCUMENTS

| 10,360,900 | B1 * | 7/2019 | Sieracki | .................. G10L 17/26 |
| 2009/0011999 | A1 * | 1/2009 | Herrmann | ........ C07K 14/43522 514/2.1 |

(Continued)

OTHER PUBLICATIONS

Adão et al., "Hyperspectral Imaging: A Review on UAV-Based Sensors, Data Processing and Applications for Agriculture and Forestry" Remote Sensing, 9, 30 pages, 1110, 2017.

(Continued)

*Primary Examiner* — Seyed H Azarian
(74) *Attorney, Agent, or Firm* — Leanne Taveggia Farrell; Westman, Champlin & Koehler, P.A.

(57) ABSTRACT

A method of determining whether to treat soybeans for soybean aphids, the method includes collecting at least one image of a soybean canopy using one or more remote sensing instruments and processing the image into spectral reflectance data and selecting from the spectral reflectance data optimal spectral wavelength bands. The selected reflectance data is classified into one of a plurality of classification groupings using a machine learned classification model. To treat or not treat the soybean canopy for aphids is determined based on the classification of the reflectance data into one of the class groupings.

16 Claims, 5 Drawing Sheets

(51) Int. Cl.
      *G01N 21/359*     (2014.01)
      *G01N 33/02*     (2006.01)

(56) References Cited

U.S. PATENT DOCUMENTS

| | | | | |
|---|---|---|---|---|
| 2012/0174246 | A1* | 7/2012 | Chaky | C12Q 1/6895 800/260 |
| 2014/0082769 | A1* | 3/2014 | Schymkowitz | A61P 35/00 800/298 |
| 2016/0232621 | A1* | 8/2016 | Ethington | G06Q 50/02 |
| 2018/0223310 | A1* | 8/2018 | Niblett | C12N 15/8279 |

OTHER PUBLICATIONS

Akbani et al., Applying support vector machines to imbalanced datasets, Springer, Berlin, Heidelberg, pp. 39-50, 2004.
Allouche et al., "Assessing the accuracy of species distribution models: prevalence, kappa and the true skill statistic (TSS)", Journal of Applied Ecology, 43: pp. 1223-1232, 2006.
Alves et al., "Soybean aphid (Hemiptera: Aphididae) affects soybean spectral reflectance", Journal of Economic Entomology, 108: pp. 2655-2664, 2015.
Alves et al., "Optimizing band selection for spectral detection of Aphis glycines Matsumura in soybean". Pest Manag. Sci., 75: pp. 942-949, 2018.
Alves et al., "Effects of foliar insecticides on leaf-level spectral reflectance of soybean", Journal of Economic Entomology, 110: pp. 2436-2442, 2017.
Bai et al., "Field-based scoring of soybean iron deficiency chlorosis using RGB imaging and statistical learning", Frontiers Plant Science, 9:1002, 13 pages, 2018.
Bajwa et al., "Soybean disease monitoring with leaf reflectance", Remote Sensing, 9: 127, 15 pages, 2017.
Beckendorf et al., "Soybean aphid feeding injury and soybean yield, yield components, and seed composition" Agronomy Journal, 100:2, pp. 237-246, 2008.
Behmann et al., "A review of advanced machine learning methods for the detection of biotic stress in precision crop protection", Precision Agric. 16: pp. 239-260, 2015.
Bueno et al., Effects of integrated pest management, biological control and prophylactic use of insecticides on the management and sustainability of soybean. Crop Prot. 30: 937-945, 2011.
Cai et al., "Feature selection in machine learning: A new perspective" Neurocomputing, 300: pp. 70-79, 2018.
Camargo et al., "Image pattern classification for the identification of disease causing agents in plants" Computers and Electronics in Agriculture, 66: pp. 121-125, 2009.
Canis, "Unmanned Aircraft Systems (UAS): Commercial outlook for a new industry", Congressional Research Service, 17 pages, 2015.
Casady et al., Precision agriculture: remote sensing and ground truthing. Univ. Missouri—Columbia. Univ. Extension. Ext. website. https://extension.missouri.edu/p/EQ453 (accessed Apr. 30, 2019), 2002.
Chang et al., "Detecting weed-free and weed-infested areas of a soybean field using near-infrared spectral data", Weed Science, 52: pp. 642-648, 2004.
Chappelle et al., "Ratio analysis of reflectance spectra (RARS): an algorithm for the remote estimation of the concentrations of chlorophyll A, chlorophyll B, and carotenoids in soybean leaves" Remote Sensing of Environment, 39: 239-247,1992.
Cui et al., Detection of soybean rust using a multispectral image sensor Sens. Instrum. Food Qual. Saf, 3: pp. 49-56, 2009.
De Farias Neto et al., "Irrigation and Inoculation Treatments that Increase the Severity of Soybean Sudden Death Syndrome in the Field" Crop Science, 46: pp. 2547-2554, 2006.
Diaz-Montano et al., "Chlorophyll loss caused by soybean aphid (Hemiptera: Aphididae) feeding on soybean" Journal of Economic Entomology, 100: pp. 1657-1662, 2007.
Elliott et al., "NDVI to detect sugarcane aphid injury to grain sorghum", Journal of Economic Entomology, pp. 1452-1455, 2015.
Elliott et al., "Airborne remote sensing to detect greenbug stress to wheat" Southwest Entomologist, 34: pp. 205-211, 2009.
Elliott et al., "Airborne multi-spectral remote sensing of Russian wheat aphid injury to wheat" Southwest Entomologish, 32: oo, 213-219, 2007.
Fehr et al., "Stages of Soybean Development", Special Report 80, Cooperative Extension Service, Iowa State Univ., Ames, IA, 13 pages, 1977.
Foody, "Status of land cover classification accuracy assessment" Remote Sensing Environment, 80: pp. 185-201, 2002.
Gates et al., "Spectral Properties of Plants" Applied Optics, 4: pp. 11-20, 1965.
Gausman et al., "Optical Parameters of Leaves of 30 Plant Species", Plant Physiol, 52, pp. 57-62, 1973.
Gazala et al., "Spectral reflectance pattern in soybean for assessing yellow mosaic disease" Indian Journal of Virological, 24: pp. 242-249, 2013.
Gitelson et al., "Relationships between leaf chlorophyll content and spectral reflectance and algorithms for non-destructive chlorophyll assessment in higher plant leaves" Journal of Plant Physiology, 160: pp. 271-282, 2003.
Gomez-Chova et al., "Mean map kernel methods for semisupervised cloud classification", IEEE Transactions on Geoscience and Remote Sensing, 48: pp. 207-220, 2010.
Govender et al., "A review of hyperspectral remote sensing and its application in vegetation and water resource studies" Water SA, 33, pp. 145-152, 2007.
Hanafi et al., "Spread and control of potato leafroll virus in Minnesota", Journal of Economic Entomology, 82: pp. 1201-1206, 1989.
Hatfield et al., "Application of spectral remote sensing for agronomic decisions", Agronomy Journal, 100: pp. S117-S131, 2008.
Henry et al., "Spectral reflectance curves to distinguish soybean from common cocklebur (*Xanthium strumarium*) and sicklepod (*Cassia obtusifolia*) grown with varying soil moisture" Weed Science, 52: pp. 788-796, 2004.
Henry et al., "Remote sensing to distinguish soybean from weeds after herbicide application", Weed Technology, 18: pp. 594-604, 2004.
Herrmann et al., "Leaf and canopy level detection of Fusarium virguliforme (sudden death syndrome) in soybean" 2018, Remote Sensing, 10: 426, 20 pages 2018.
Hill et al., "A new soybean aphid (Hemiptera: Aphididae) biotype identified", Journal of Economic Entomology, 103: pp. 509-515, 2010.
Hill et al., "Resistance to the soybean aphid in soybean germplasm", Crop Science, 44: pp. 98-106, 2004.
Hodgson et al., "Management recommendations for soybean aphid (Hemiptera: Aphididae) in the United States", Journal of Integrated Pest Management, 3: 10 pages, 2012.
Hodgson et al., "Enumerative and binomial sequential sampling plans for soybean aphid (Homoptera: Aphididae) in soybean" Journal of Economic Entomology, 97: pp. 2127-2136, 2004.
Hsu et al., "A practical guide to support vector classification", In: Technical Report. Department of Computer Science, National Taiwan University, Taipei 106, Taiwan, 12 pages, 2008.
Hurley et al., "Value of neonicotinoid seed treatments to US soybean farmers" Pest Manag. Sci., 73: pp. 102-112, 2017.
Jackson et al., "Vegetation water content mapping using Landsat data derived normalized difference water index for corn and soybeans", Remote Sensing of Environment, 92: pp. 475-482, 2004.
Jain et al., "Data clustering: a review", ACM Computing Survey, 31: pp. 264-323, 1999.
Klement et al., "Reliability of Cross-Validation for SVMs in High-Dimensional, Low Sample Size Scenarios", pp. 41-50. In Artif. Neural Networks—ICANN 2008. Springer Berlin Heidelberg, Berlin, Heidelberg, 2008.
Koch et al., "Biology and economics of recommendations for insecticide-based management of soybean aphid" Plant Health Progress, 17: pp. 265-269, 2016.

(56) References Cited

OTHER PUBLICATIONS

Koger et al., "Wavelet analysis of hyperspectral reflectance data for detecting pitted morningglory (*Ipomoea iacunosa*) in soybean (*Glycine max*)", Remote Sensing Environment, 86: pp. 108-119, 2003.
Kotsiantis et al., "Supervised machine learning: A review of classification techniques", Emerging artificial intelligence applications in computer engineering, 160: pp. 3-24, 2007.
Lelong et al., "Assessment of unmanned aerial vehicles imagery for quantitative monitoring of wheat crop in small plots", Sensors (Basel). 8: pp. 3557-3585, 2008.
Liaghat et al., "A Review: The role of remote sensing in precision agriculture", American Journal of Agricultural and Biological Sciences, 5: pp. 50-55, 2010.
Ma et al., "Early prediction of soybean yield from canopy reflectance measurements", Agronomy Journal, 93: pp. 1227-1234, 2001.
Marston et al., "Detection of stress induced by soybean aphid (Hemiptera: Aphididae) using multispectral imagery from unmanned aerial vehicles", Journal of Economic Entomology, 29 pages, 2019.
Maxwell et al., "Implementation of machine-learning classification in remote sensing: an applied review", International Journal of Remote Sensing, 39: pp. 2784-2817, 2018.
Menke, "Using Spectral Reflectance in Soybean Breeding: Evaluating Genotypes for Soybean Sudden Death Disease Resistance and Grain Yield", M.S. thesis, Kansas State University, Manhattan, 111 pages, 2018.
Mensah et al., "Resistance to soybean aphid in early maturing soybean germplasm", Crop Science, 45: pp. 2228-2233, 2005.
Mirik et al., "Reflectance characteristics of Russian wheat aphid (Hemiptera: Aphididae) stress and abundance in winter wheat", Computers and Electronics in Agriculture, 57: pp. 123-134, 2007.
Mirik et al., "High spectral and spatial resolution hyperspectral imagery for quantifying Russian wheat aphid infestation in wheat using the constrained energy minimization classifier", Journal of Applied Remote Sensing, 8: 083661-1-083661-14, 2014.
Mountrakis et al., "Support vector machines in remote sensing: A review" ISPRS Journal of Photogrammetry Remote Sensing, 66: pp. 247-259, 2011.
Nagasubramanian et al., "Hyperspectral band selection using genetic algorithm and support vector machines for early identification of charcoal rot disease in soybean stems", Plant Methods, 16: 86, 16 pages, 2018.
Nebiker et al., "Light-weight multispectral sensor for micro UAV—Opportunities for very high resolution airborne remote sensing", International Archives of the Photogrammetry, Remote Sensing and Spatial Information Sciences, 37(B1): pp. 1193-1200, 2008.
Nellis et al., "Remote Sensing of Cropland Agriculture", The SAGE Handbook of Remote Sensing, SAGE Publications, Inc., pp. 368-380, 2009.
Nutter et al., Use of remote sensing to detect soybean cyst nematode-induced plant stress, Journal of Nematology, 34: pp. 222-231, 2002.
Ollinger, "Sources of variability in canopy reflectance and the convergent properties of plants", New Phytologist, 189: 375-394, 2011.
Olson et al., "Farmers' awareness and use of IPM for soybean aphid control: Report of survey results for the 2004, 2005, 2006, and 2007 crop years", Staff Paper Series Report, Department of Applied Economics, University of Minnesota, St. Paul, 31 pages, 2008.
Pal et al., "Feature selection for classification of hyperspectral data by SVM", IEEE Transactions on Geoscience and Remote Sensing, 45 pages, 2010.
Pinter et al., "Remote sensing for crop management", Photogrammetric Engineering & Remote Sensing, 69: pp. 647-664, 2003.
Prabhakar et al., "Use of ground based hyperspectral remote sensing for detection of stress in cotton caused by leafhopper (Hemiptera: Cicadellidae)", Computers and Electrontronics Agriculture, 79: pp. 189-198, 2011.

Prabhakar et al., "Hyperspectral indices for assessing damage by the solenopsis mealybug (Hemiptera: Pseudococcidae) in cotton", Computers and Electronics in Agricultur, 97: pp. 61-70, 2013.
Ragsdale et al., "Economic threshold for soybean aphid (Hemiptera: Aphididae)", Journal of Economic Entomology, 100: pp. 1258-1267, 2007.
Ragsdale et al., "Ecology and management of the soybean aphid in North America", Annual Review of Entomology, 56: pp. 375-399, 2011.
Rouse et al., "Monitoring the vernal advancement and retrogradation (green wave effect) of natural vegetation", Texas A&M University, Remote Sensing Center, College Station, TX, 87 pages, 1973.
Roy et al., "Sudden Death Syndrome of Soybean", Plant Disease, 81: pp. 1100-1111, 1997.
Ruppel, "Cumulative insect-days as an index of crop protection" Journal of Economic Entomology, 76: pp. 375-377, 1983.
Skakun et al., "Early season large-area winter crop mapping using MODIS NDVI data, growing degree days information and a Gaussian mixture model", Remote Sensing of Environment, 195: pp. 244-258, 2017.
Song et al., "Returns to integrated pest management research and outreach for soybean aphid", Journal of Economic Entomology, 102: pp. 2116-2125, 2009.
Summy et al., "Using color infrared imagery to detect sooty mold and fungal pathogens of glasshouse-propagated plants", HortScience, 43: pp. 1485-1491, 2008.
Sun et al., "Classification of imbalanced data: a review", International Journal of Pattern Recognition and Artificial Intelligence, 23: pp. 687-719, 2009.
Thomlinson et al., "Coordinating methodologies for scaling landcover classifications from site-specific to global: steps toward validating global map products", Remote Sensing Environ, 70: pp. 16-28, 1999.
Tilmon et al., "Biology of the soybean aphid, Aphis Glycines (Hemiptera: Aphididae) in the United States", Journal of Integrated Pest Management, 2: pp. 1-7, 2011.
(USDA-NASS) United States Department of Agriculture—National Agricultural Statistics Service. 2018. Agricultural statistics 2018. https://www.nass.usda.gov/Publications/Ag_Statistics/2018/Complete%20Publication.pdf (accessed Apr. 30, 2019).
Vigier et al., "Narrowband vegetation indexes and detection of disease damage in soybeans" IEEE Geoscience and Remote Sensing Letters, 1: pp. 255-259, 2004.
Way et al., "Effect of finite sample size on feature selection and classification: a simulation study", Medical Physics, 37: pp. 907-920, 2010.
Westphal et al., "Contributions of Fusarium virguliforme and Heterodera glycines to the Disease Complex of Sudden Death Syndrome of Soybean", PLoS One, 9: 13 pages, 2014.
Yao et al., "Unmanned aerial vehicle for remote sensing applications—a review", Remote Sensing, 11: 1443, 22 pages, 2019.
Yuan et al., "Spectral analysis of winter wheat leaves for detection and differentiation of diseases and insects", Field Crops Research, 156: pp. 199-207, 2014.
Zhang et al., "The application of small unmanned aerial systems for precision agriculture: a review", Precision Agriculture, 13: pp. 693-712, 2012.
Zhang et al., "Scaling up Kernel SVM on Limited Resources: A Low-rank Linearization Approach", Proceedings of the 15th International Conference, on Artificial Intelligence and Statistics, pp. 1425-1434, 2012.
Hodgson et al., Field validation of speed scouting for soybean aphid, Plant Management Network, Crop Management, 6(1), 9 pages, 2007.

\* cited by examiner

REMOTE-SENSING-BASED DETECTION OF SOYBEAN APHID INDUCED STRESS IN SOYBEAN

This invention was made with government support under 2016-70006-25828 awarded by the National Institute of Food and Agriculture, USDA. The government has certain rights in the invention.

BACKGROUND

When certain forms of stress cause sufficient changes in plant morpho-physiology and biochemistry, there are often corresponding detectable changes to plant foliar reflectance. Some forms of stress that affect soybean spectral reflectance include mineral deficiencies, drought, soybean cyst nematode, soybean rust, sudden death syndrome, scelerotinia stem rot, charcoal rot, and soybean aphids, with soybean aphids being the most economically injuring pest in the North Central Region of the United States where 70% of U.S. soybean production takes place. Not only does the soybean aphid use piercing-sucking mouthparts to remove photosynthate from the plant through the phloem and cause yield losses of soybean up to 40%, if left untreated, soybean aphids also can transmit viral plant diseases and affect the performance of other soybean pests.

Reflectance data from multispectral bands improve the ability to make inferences about crop stress. The increasing availability of remote hyperspectral sensors, which measure hundreds or thousands of continuous narrowband wavelengths, has drastically increased the amount of information available for detecting specific forms of crop stress.

SUMMARY

A method of determining whether to treat soybeans for soybean aphids includes collecting at least one image of a soybean canopy using one or more remote sensing instruments, processing the image into spectral reflectance data and selecting from the spectral reflectance data optimal spectral wavelength bands. The selected reflectance data is classified into one of a plurality of classification groupings using a machine learned classification model. The classification groupings include at least a first group that corresponds with a count of aphids that is below a threshold count of aphids and a second group that corresponds with a count of aphids that is above the threshold count of aphids. To treat or not treat the soybean canopy for aphids is determined based on the classification of the reflectance data into one of the class groupings.

A computer system includes a memory storing spectral reflectance data for a soybean canopy and a processor that executes instructions to perform steps. The steps include selecting from the spectral reflectance data optimal spectral wavelength bands, classifying the selected reflectance data into one of a plurality of classification groupings using a machine learned classification model trained with spectral reflectance data and corresponding actual aphid counts and determining whether to treat or not treat the soybean canopy for aphids based on the classification of the reflectance data into one of the class groupings.

A method includes receiving reflectance data for an area of a soybean field and selecting from the spectral reflectance data optimal spectral wavelength band. The selected reflectance data is classified into one of a plurality of classification groupings using a machine learned classification model trained with spectral reflective data in the select optimal spectral wavelength bands and corresponding actual aphid counts. To treat or not treat the soybean canopy for aphids is determined based on the classification of the reflectance data into one of the class groupings.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

The U.S. continues to lead the world in soybean production and the north-central U.S. accounts for over 75% of the nation's production. Over the past two decades, however, there has been a dramatic change in soybean production in the north-central U.S., due to an invasive species, the soybean aphid. Prior to the invasion by soybean aphid in 2000, there were few insects reaching levels causing economic injury to soybean and fewer than 0.1% of soybean fields in the north-central U.S. were sprayed with insecticide. By 2006, there was more than a 130-fold increase of insecticide applications to soybean in the region. This increase was largely due to the soybean aphid's ability to rapidly reproduce and reduce soybean yields.

Soybean aphid damages soybean by extracting photosynthate. This feeding can decrease yield through plant stunting, decreased leaf area, reduced pod and seed number, decreased seed weight and oil concentrations, and even plant death. Furthermore, soybean aphids excrete honeydew on leaf surfaces while feeding, which can promote the growth of sooty mold and further reduce yields by inhibiting photosynthesis. Soybean aphid infestations left untreated have been documented to reduce soybean yields by more than 40% and is considered the most economically injuring insect pest of soybean in the north-central U.S.

Figure 1:
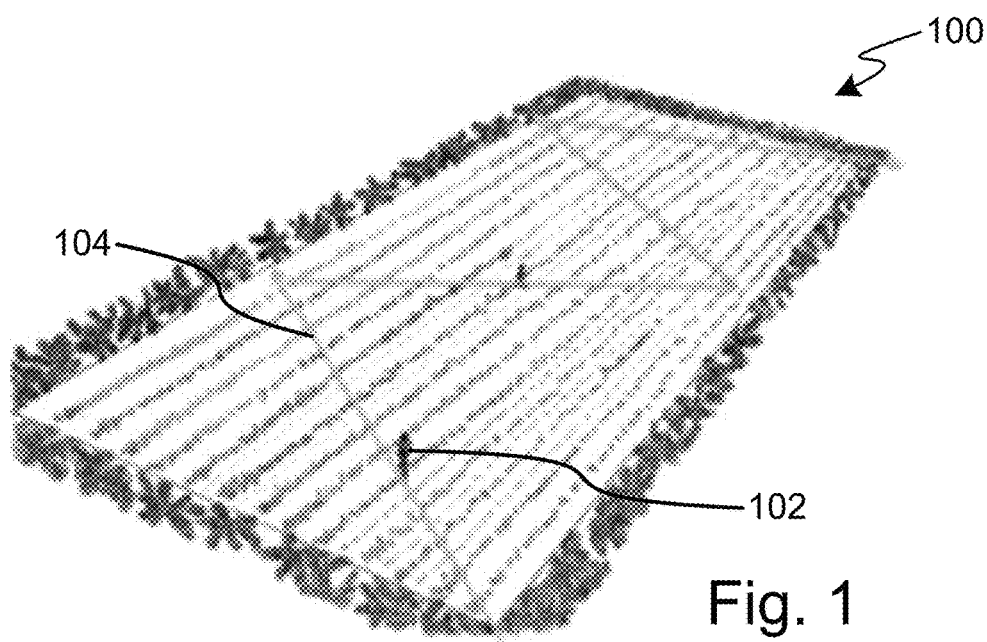
FIG. 1 provides a diagram of a soybean field or canopy and a manual method of scouting the field for soybean aphids.

As illustrated in FIG. 1, current management recommendations involve routine manual scouting of soybean fields, such as soybean field or canopy 100, to monitor soybean aphid populations. Routine manual scouting is needed because widespread outbreaks of soybean aphid are erratic, and the timing of colonization can fluctuate. When aphid populations reach an economic threshold of 250 aphids per plant, chemical control is recommended to prevent aphids from reaching the economic injury level of ~674 aphids per plant. In FIG. 1, a scout 102 walks a zig-zag pattern 104 in exemplary field or canopy 100 counting the soybean aphids on roughly 20-40 plants per field. As illustrated, this conventional scouting practice only covers a small portion of field 100, still creating the potential to miss areas heavily infested with soybean aphid.

While many farmers follow these recommendations, some farmers are reluctant to adopt these practices because the scouting process can be arduous and time consuming. A more efficient, speed scouting sampling plan exists, but further testing of this method found that correct management decisions were attained only 79% of the time, the other 21% of the time decisions to apply insecticide were made before aphid populations reached the economic threshold. The difficulty associated with counting aphids within a large field of densely planted soybean and the lack of coverage provided by current scouting methods has led some farmers to use prophylactic applications of insecticides rather than base chemical treatment on estimates of aphid populations in the field. This prophylactic method of control can be economically and environmentally detrimental. Incorporating remote sensing with a technique for making a treatment decision offers the potential to improve management of soybean aphid by decreasing the effort and cost of scouting while increasing field coverage, which may increase adoption of management practices based on estimates of in-field pest abundance and thereby decrease unnecessary pesticide applications.

Remote sensing for agriculture includes passively obtaining information about the health of a crop, within field variability, by relating electromagnetic, or spectral, reflectance to plant biological components and physiology, such as foliar pigment content, cellular structure, water content, as well as canopy coverage and architecture. One of the most commonly used spectral indices for remote sensing in agriculture is the normalized difference vegetation index (NDVI). The NDVI is particularly helpful because it combines red reflectance with near-infrared reflectance. Red reflectance is an indicator of chlorophyll content of the plant canopy and active photosynthesis and near-infrared reflectance (NIR) provides information about the cellular structure and intracellular air spaces within leaves, overall canopy coverage, and above ground biomass. When these wavelengths are combined in an index, like NDVI, it provides a measure of overall plant health and has frequently been correlated with crop yield.

Figure 2:
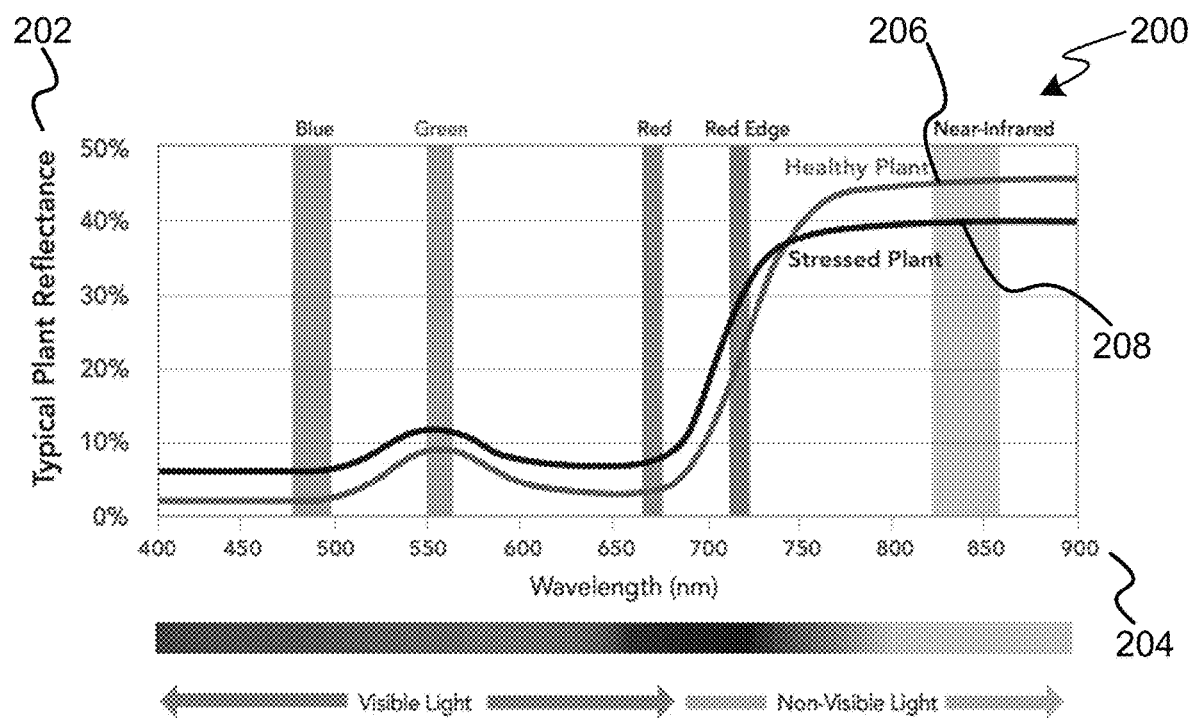
FIG. 2 provides a graph of plant reflectance versus wavelength of light for a healthy plant and a stressed plant.

FIG. 2 illustrates a general graph 200 of plant reflectance 202 versus wavelength of light 204. As illustrated, the spectral response curve 206 of a healthy plant and the spectral response curve 208 of a stressed plant are different. The stressed plant has significant decreases in NDVI values or red edge to NIR values relative to the healthy plant.

Different forms of crop stress, such as nutrient deficiencies, soybean cyst nematode, soybean sudden death syndrome, soybean aphids, weed pressure and drought stress affect the spectral reflectance of the plants, which can be detected through remote sensing. Remote sensing in agriculture may use ground-based systems, which are often restricted by small mapping swaths and limited transportability, satellites or piloted aircraft which have been expensive, low-resolution, and limited by atmospheric conditions and orbital periods. More recently, unmanned aerial vehicles (UAVs) equipped with ultra-high spatial resolution multispectral sensors have become increasingly available to consumers and promise low-cost near real-time image acquisition for use in agricultural applications. The use of UAV's for agriculture can provide high temporal and spatial resolution information on soils, crop nutrients, pest, moisture and yield.

For example, to capture canopy spectral reflectance measurements from a soybean field using a UAV, an optical-mechanical sensor, such as a multispectral camera, may be attached to a UAV via a vibration plate to minimize distortion in the imagery caused by UAV movement. The multispectral camera may be equipped with a standard red, green and blue color light sensor (RGB), a narrowband red sensor (625±12.5 nm), a narrowband near-infrared sensor (775±12.5 nm) and a broadband near-infrared sensor (825±100 nm). Such bands are known for detecting soybean aphid-induced stress. UAV flights may be performed in a cross-grid pattern at a low altitude, such as an altitude of 40-50 meters. To minimize the effect of solar angle and showing on the crop canopy, imagery should be recorded between 10:00 am and 2:00 pm. In addition, to minimize atmospheric effects, imagery should be recorded when light conditions are uniform, such as cloudless days or at times when no visible clouds were moving between the sun and the crop canopy.

While remote sensing, such as remote sensing using UAVs, offers a way to improve adoption of scouting programs for soybean aphid by decreasing human effort and improving spatial coverage, in order for remote sensing to be useful it should be used to make actionable determinations. Under one embodiment, machine-learning classification is used to convert complex reflectance data into "treat soybean" or "do not treat soybean" decisions.

Machine-learning classification methods generally fall into two categories: unsupervised and supervised learning. Unsupervised learning typically involves clustering algorithms, where unlabeled data are grouped into one or more classes with the goal of discovering unknown, but useful classes of items. In supervised learning, samples of data are labeled as classes and are used to train a model that can predict the class of or generalize future samples.

Figure 3:
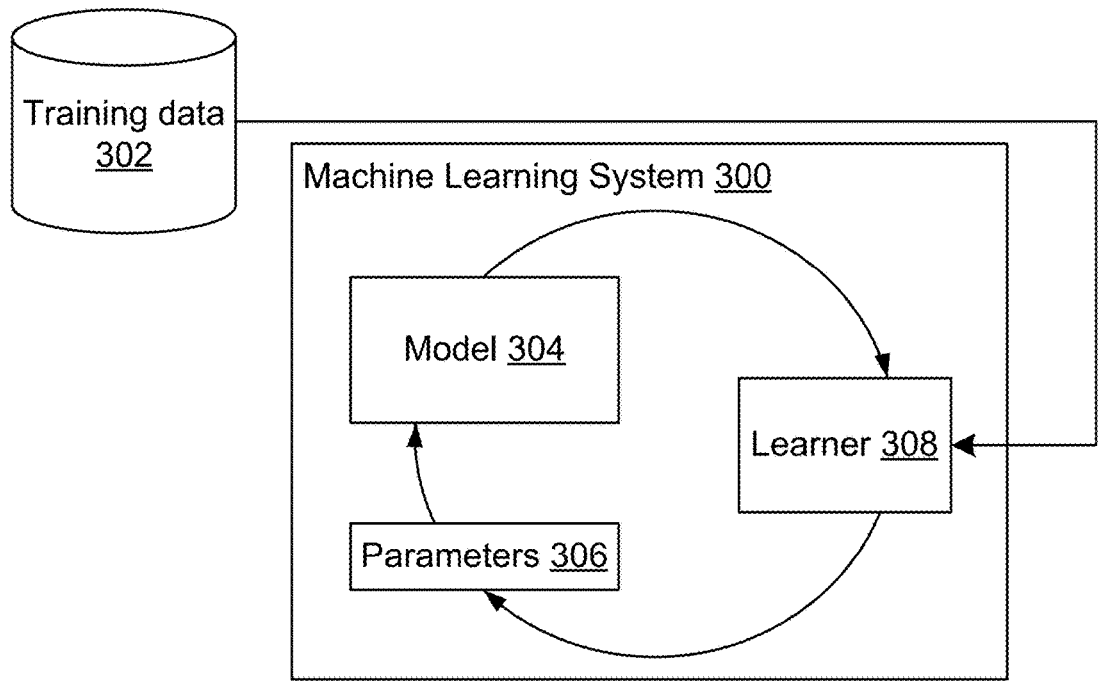
FIG. 3 provides a block diagram of a machine learning system according to an embodiment.

FIG. 3 illustrates a block diagram of a supervised machine learning system 300 using training data 302 according to one embodiment. Machine learning system 300 includes a model 304 that makes predictions or identifications, parameters 306, which are the signals or factors used by the model to form decisions and a learner 308 that adjusts the parameters, and in turn model 304, by looking at the differences between predictions and actual outcome.

There are many accepted methods of supervised machine-learning classification (e.g., including k-nearest neighbors (k-NN), single decision trees (DTs), Random Forests (RF), artificial neural networks (ANN), and support vector machines (SVMs)) that often outperform parametric maximum likelihood classifiers. Each of these methods has its tradeoffs, which can include requiring a large training set, large storage requirements, sensitivity to irrelevant features and noise, poor interpretability, slow learning and classification speed, and potential to overfit model 304, which affects the capacity to generalize well with future samples. Under one embodiment, machine learning system 300 comprises a linear support vector machine to classify reflectance data into classes based on an economic threshold count of 250 aphids per plant and using optimized wavelengths or features to generate an accurate model without overfitting the data.

Linear support vector machines aim to find an optimal boundary or hyperplane in feature space to linearly separate classes, have a high degree of accuracy, are fairly tolerant of redundant attributes, are able to handle small training data sets, are relatively robust to overfitting, and generally do well with imbalanced data. Linear support vector machines, like most machine-learning classifiers, are susceptible to imbalanced training data often favoring correct classification of the dominant class. There are multiple methods to address this problem of imbalanced training data including undersampling (reducing the overall size of the training set by excluding samples from the majority class), oversampling (synthetically increasing the minority class), and penalized models (using weighting to adjust for class imbalances).

All combinations of a select four wavelengths (720, 750, 780, and 1,010 nm) trained with SVM models classify test samples into above the economic threshold of 250 aphids (treat) or below the threshold (no-treat) with over 80% accuracy, which is a significant improvement over the no information rate. However, accuracy alone can be misleading especially with imbalanced data.

There are important differences in both sensitivity, specificity and accuracy of, for example, models 1 (780 nm), 2 (780 and 1,010 nm), 3 (780, 1,010, and 720 nm), and 4 (780, 1,010, 720, and 750 nm). Sensitivity is a measure of true positive classification (in this case correctly assigning samples to a class grouping that corresponds to a count of aphid that is below the economic threshold count). Specificity is a measure of true negative classification (correctly classifying samples to a class grouping that corresponds to a count of aphids that is above the economic threshold count). While the SVM model 1 using only 780 nm to predict classes attained the highest sensitivity of all models, this model has the worst specificity and correctly classified samples above the economic threshold only 56% of the time. Both models 3 (780, 1,010, and 720 nm) and 4 (780, 1,010, 720, and 750 nm) had the same accuracy as model 1 (780 nm); however, they both had higher specificity and were capable of correctly classifying samples above the economic threshold nearly 72% of the time, suggesting they were better models.

Overall, model 2 (780 and 1,010 nm) performed the best, with an accuracy of 89.4%, a sensitivity of 91.6% and a specificity of 81.3%. Furthermore, this model attained the highest Cohen's Kappa (a statistic that evaluates observed accuracy against expected accuracy taking into consideration agreement occurring by random chance), suggesting a better fit which is particularly helpful in instances of imbalanced data. The pairwise Bonferroni-adjusted t-test of Kappa values also suggested that models 2 (780 and 1,010 nm), 3 (780, 1,010, and 720 nm), and 4 (780, 1,010, 720, and 750 nm) performed significantly better than model 1 (780 nm), but were not statistically different from each other.

Figure 4:
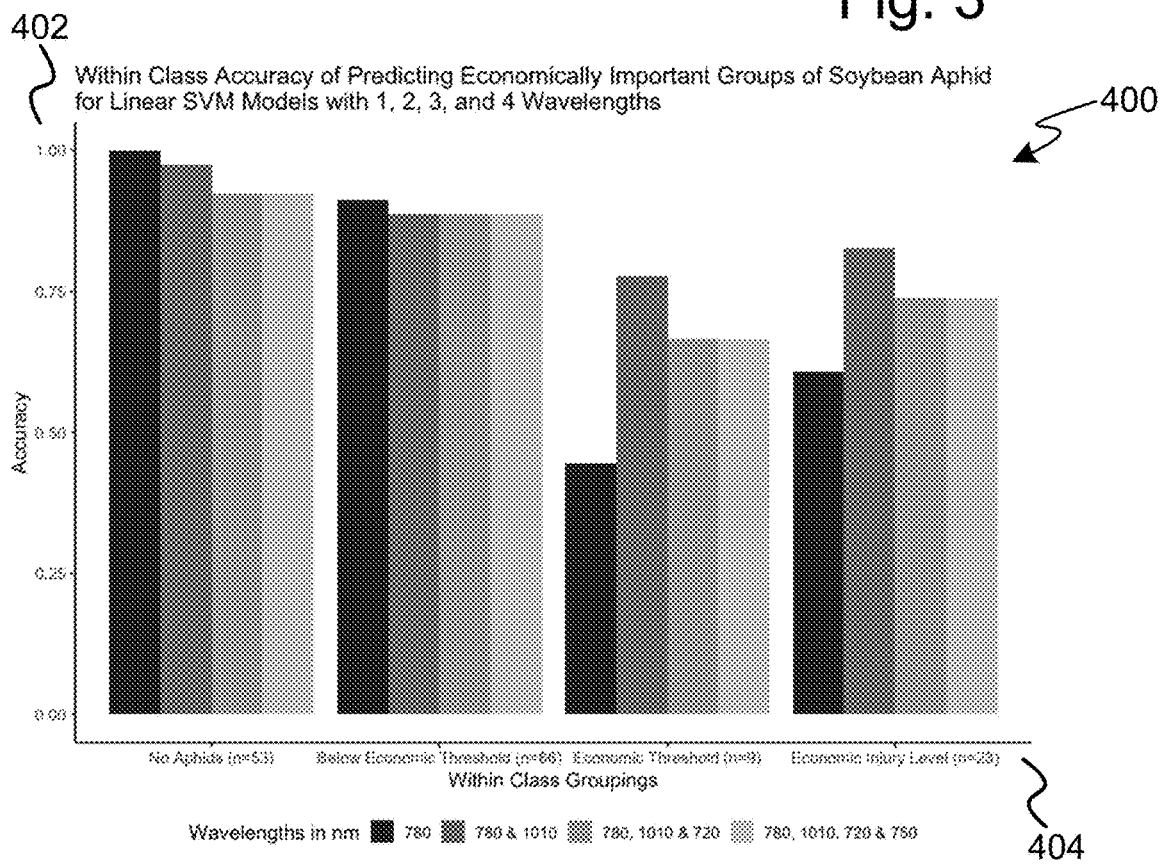
FIG. 4 provides a graph illustrating the accuracy of machine learning models of soybean aphid classifying groups.

Accuracy decreases in groups closer to the economic threshold of 250 aphids per plant. The best model, model 2 (780 and 1,010 nm) showed only a 77% accuracy for samples above the economic threshold, but below the economic injury level, compared to 83% accuracy for samples that were above the economic injury level. Similarly, within the below threshold class, accuracy for samples with no aphids was better than samples with aphid populations below the economic threshold. FIG. 4 illustrates a graph 400 showing accuracies 402 for linear support vector machine models trained to classify hyperspectral test samples of soybean aphid stressed plants class groupings 404 as above or below an economic threshold count of aphids with between a select 1 and 4 wavelengths.

It is common, however, for multiple forms of stress, not just soybean aphid stress, to occur simultaneously within soybean fields. Even though these different forms of stress may affect different specific biophysical and biochemical processes within plants, many times different forms of stress can affect similar portions of the electromagnetic spectrum confounding the ability to determine the cause of the stress from reflectance data. Furthermore, some other common forms of stress to soybean plants such as diseases, herbicide damage, and drought stress affect red edge and NIR reflectance.

One common form of stress encountered in soybean in the north-central United States that is also known to affect NIR reflectance is sudden death syndrome (SDS) caused by the fungal pathogen *Fusarium virguliforme*. *Fusarium virguliforme* is a soil-borne pathogen that infects the roots of soybean plants and can cause root rot, as well as the production of phytotoxins that can be translocated to foliar tissues and cause interveinal chlorosis and necrosis, and even premature defoliation and death in severe cases. Sudden death syndrome has been shown to cause yield losses as great as 40% and is continuing to increase in both spatial distribution and economic importance.

Like soybean aphid, SDS has been shown to decrease soybean reflectance values in the NIR spectrum, but SDS was shown to also increase reflectance in the visible portion of the spectrum, which is not typically observed with soybean aphid. In yet another embodiment, machine learning system 300 is a linear support vector machines that is used to determine whether SDS-induced changes to reflectance data can be differentiated from soybean aphid-induced stress and the effects of SDS on the spectral classification of soybean reflectance for soybean aphid.

The first model trained was a linear SVM model including all three classes: healthy, soybean aphid infested, and SDS. An additional SVM model was trained using identical parameters to the prior model, however in this model only the classes healthy or infested with soybean aphid were used for training. During the validation testing of this model, however, all samples in the class SDS were included to determine how classification accuracy of the soybean aphid class was affected by the presence of SDS as a confounding factor.

Feature selection indicated that the wavelengths 789, 711, 1,010, 1,044, and 919 nm were the optimal subset of features to predict the classes of test data. Two of these wavelengths (789 and 1,010 nm) are nearly identical to wavelengths identified previously to detect soybean aphid-induced stress. While overall accuracy was only 77.4% for the multiclass classification, which is lower than the suggested minimum for remote sensing-based vegetation mapping, the results were still a significant improvement over the no information rate. Additionally, classifications of healthy and soybean aphid infested classes were more accurate than the SDS class, with 82.8%, 91.7%, and 50% accuracies, respectively. Because the soybean aphid infested class was still predicted with a specificity of 95.1%, there may only be a minimal reduction in accuracy due to the presence of SDS within soybean fields. This potentially suggests SVM-based classification methods for soybean aphid infestation using remote sensing may be tolerant to the confounding factor of SDS.

A second linear SVM model was trained to test SDS as a confounding factor and was trained using only the classes of soybean aphid and healthy plots. This second linear SVM model selected 772 and 1,000 nm, as the optimal subset of features for classification, which was very similar to previously reported wavelengths for detection of soybean aphid infested plots. When SDS samples were included in the validation testing of the second linear SVM model there was a much lower overall accuracy of 54.2% because the model was not trained to handle the additional class of SDS. For assessing the potential confounding effect of SDS, the metrics of interest from this model are the number of samples belonging to the class SDS being classified as false positives for the soybean aphid infested class, and the reduced specificity of the soybean aphid infested class. The confounding factor testing in this model classified 19.4% of the 31 samples belonging to the class SDS as soybean aphid infested, which was greater than the 8.3% of samples misclassified in the same manner when tested with the multiclass model. This is important because while the multiclass model may not have been suitable for the detection of SDS, it may have utility in minimizing false positives for soybean aphid. These results suggest the classification of soybean aphid-induced stress is, at a minimum, semi-tolerant of extraneous stressors, but should be ground truthed to obtain the optimal management decisions.

Linear SVMs are capable of classifying aphid-induced stress to soybean plants using spectral reflectance at a high level of accuracy (>85%), which should be sufficient for vegetation mapping even in the presence of low levels of a potentially confounding plant disease. While the results indicated that the SDS class was not capable of being classified at a level necessary for remote sensing-based vegetation mapping, we did find that including SDS in a multiclass model reduced the instances of misclassifying SDS as soybean aphid induced stress. While two wavelengths may be sufficient for classifying soybean aphid with a high degree of accuracy, including additional wavelengths for the discrimination of other confounding stressors may produce more robust results, even if classification accuracies of the other stressors are relatively poor.

Figure 5:
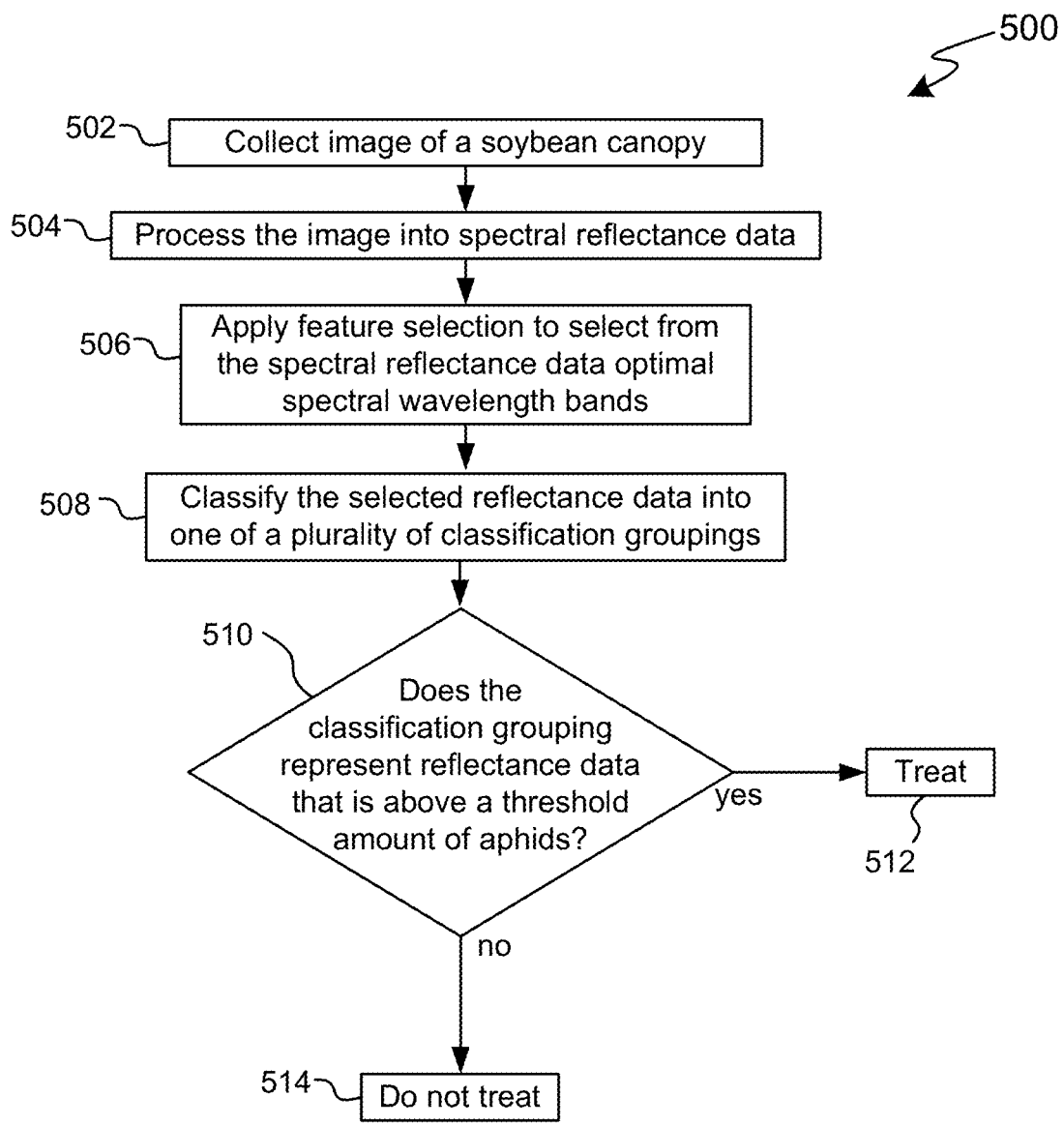
FIG. 5 provides a flow diagram of a method of determining whether to treat soybeans for soybean aphids according to an embodiment.
Figure 6:
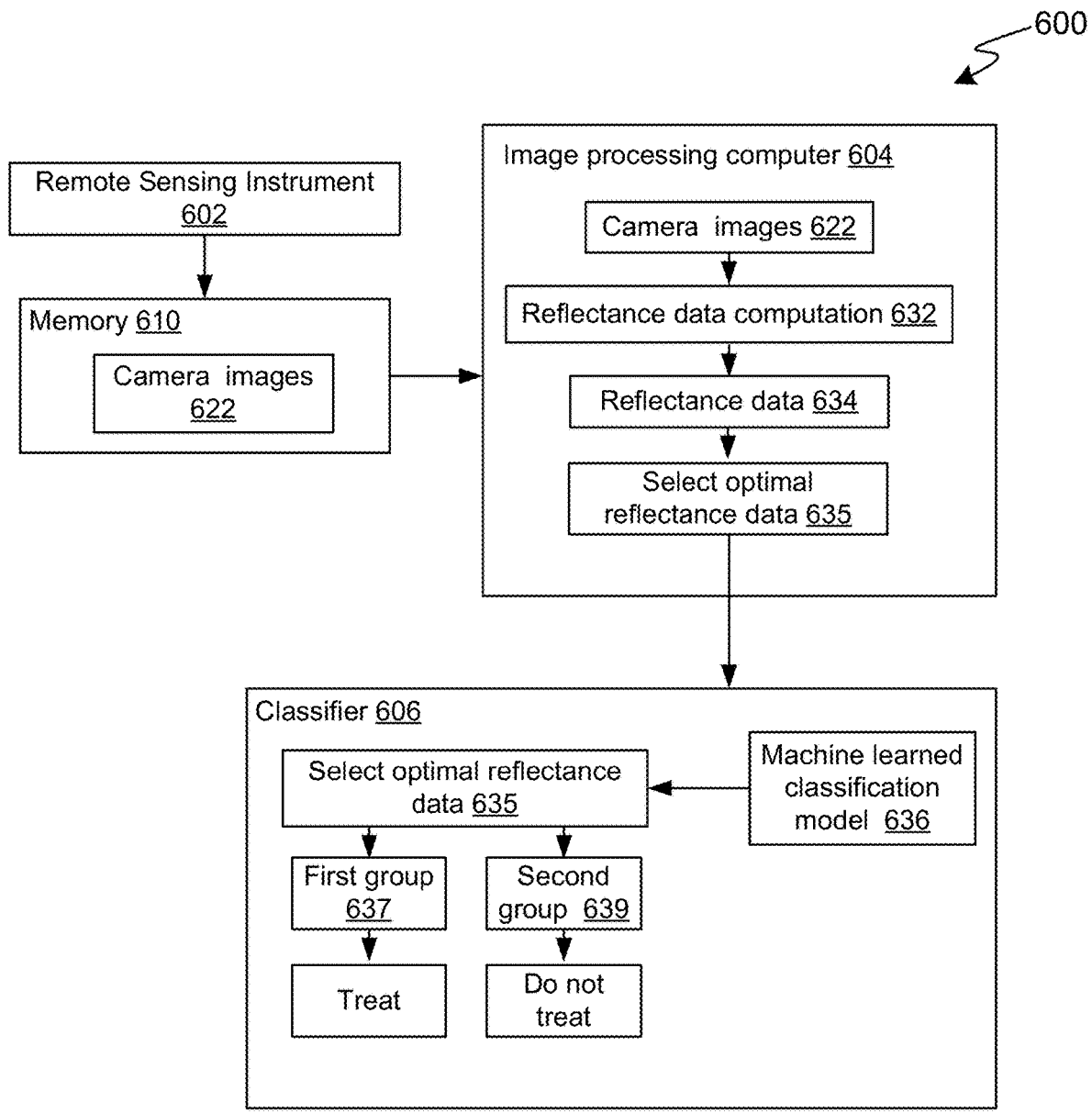
FIG. 6 provides a block diagram of a system according to an embodiment.

FIG. 5 is a flow diagram 500 of a method of determining whether to treat soybeans for soybean aphids and FIG. 6 provides a block diagram 600 of elements used to perform the steps of FIG. 5, in accordance with one embodiment.

In step 502 of FIG. 5, image data is collected by a remote sensing instrument 602 from a soybean canopy or field of soybean plants. Remote sensing instrument 602 can be mounted to ground, aerial (either a low altitude UAV or high altitude piloted aircraft), or satellite platforms, each having, as previously discussed, a unique set of advantages and limitations for use in agriculture. In accordance with one embodiment, remote sensing instrument 602 is one or more cameras consisting of an array of sensors that are capable of sensing light of a desired wavelength or band of wavelengths to form image data referred to as camera images 622. Camera images 622 are stored in a memory 610.

Periodically or in real-time, memory 610 provides image(s) 622 to image processing computer 604, which stores camera image(s) 622 in a memory in computer 604. Images 622 may be provided to image processing computer 604 over a wireless connection, a wired connection or a combination of both depending on the type of remote sensing platform.

At step 504, camera image(s) 622 are converted or processed into spectral reflectance data 634 by a reflectance data computation module 632. For example, canopy relative reflectance samples may be processed using spline interpolation in ViewSpec Pro version 6.2 (ASD ViewSpec Pro™ User Manual, ASD Inc., Boulder, Colo., USA) resulting in 2,151 narrow-band (i.e., 1 nm) wavelengths and 751 narrow-band wavelengths. Because of the large sets of reflectance data 634, at step 506 feature selection, in the form of selecting certain optimal spectral wavelength bands previously determined to be optimal in detecting soybean aphid-induced stress and/or that eliminates false positives for the soybean aphid infestation, is applied resulting in select optimal reflectance data 635. Such an application removes irrelevant and redundant features, thereby reducing both data dimensionality and processing time. For example, optimal spectral wavelength bands may be 720, 750, 780, and 1,010 nm wavelengths for soybean aphid-induced stress or 789, 711, 1,010, 1,044, and 919 nm wavelengths for both soybean aphid-induced stress and the elimination of false positives of soybean aphid infestation.

At step 508, select optical reflectance data 635 is classified into one of a plurality of classification groupings by a classifier 606. In FIG. 6, classifier 606 uses a machine learned classification model 636, such as the model 304 trained by training data 302 in FIG. 3, to classify the select optical reflectance data 635 into one of a plurality of classification groupings. In a first group 637, the select reflectance data corresponds with a count of aphids that is below a threshold count of aphids. In a second group 639, the select reflectance data corresponds with a count of aphids that is above the threshold count of aphids. As previously described, the threshold amount of aphids may be 250 aphids per plant. Machine learned classification model 636 may be trained with spectral reflectance data in the optimal spectral wavelength bands for soybean aphid-induced stress and corresponding actual aphid counts. In another embodiment, machine learned classification model 636 may be trained with spectral reflectance data in the optimal spectral wavelength bands for both soybean aphid-induced stress and the elimination of false positives of soybean aphid infestation as well as corresponding actual aphid counts.

At step 510, based on the classification, it is determined whether the reflectance data is above the threshold count of aphids. If yes, then flow diagram 500 proceeds to block 512 and the soybean canopy is to be treated. If no, then flow diagram 500 proceeds to block 514 and the soybean canopy is not to be treated.

Figure 7:
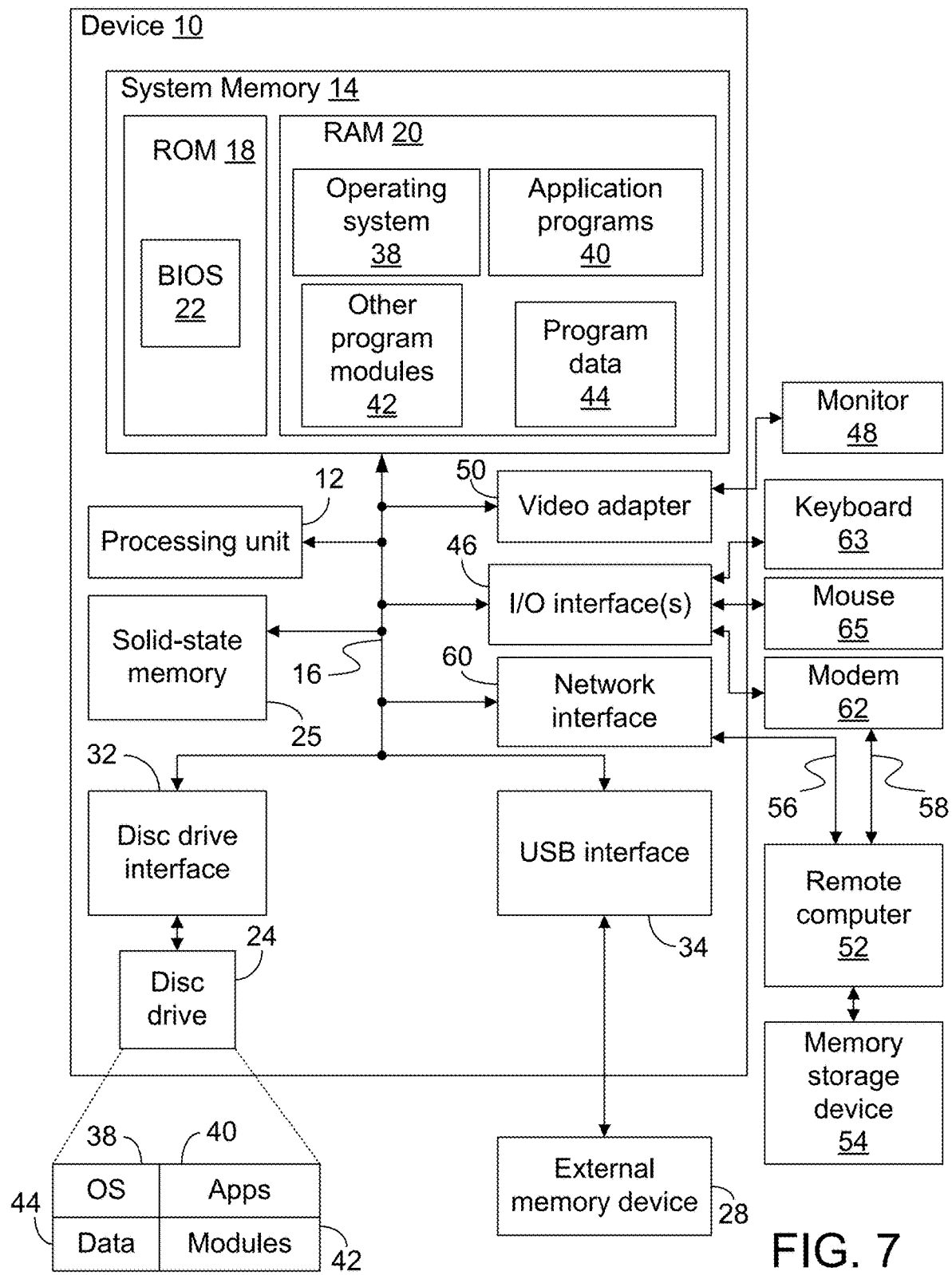
FIG. 7 provides a block diagram of elements used to implement the system illustrated in FIG. 6.

FIG. 7 provides an example of a computing device 10 that can be used as a server or client device in the embodiments above. Computing device 10 includes a processing unit 12, a system memory 14 and a system bus 16 that couples the system memory 14 to the processing unit 12. System memory 14 includes read only memory (ROM) 18 and random access memory (RAM) 20. A basic input/output system 22 (BIOS), containing the basic routines that help to transfer information between elements within the computing device 10, is stored in ROM 18. Computer-executable instructions that are to be executed by processing unit 12 may be stored in random access memory 20 before being executed.

Embodiments of the present invention can be applied in the context of computer systems other than computing device 10. Other appropriate computer systems include handheld devices, multi-processor systems, various consumer electronic devices, mainframe computers, and the like. Those skilled in the art will also appreciate that embodiments can also be applied within computer systems wherein tasks are performed by remote processing devices that are linked through a communications network (e.g., communication utilizing Internet or web-based software systems). For example, program modules may be located in either local or remote memory storage devices or simultaneously in both local and remote memory storage devices. Similarly, any storage of data associated with embodiments of the present invention may be accomplished utilizing either local or remote storage devices, or simultaneously utilizing both local and remote storage devices.

Computing device 10 further includes an optional hard disc drive 24 and an optional external memory device 28. External memory device 28 can include an external disc drive or solid state memory that may be attached to computing device 10 through an interface such as Universal Serial Bus interface 34, which is connected to system bus 16. Hard disc drive 24 is connected to the system bus 16 by a hard disc drive interface 32. The drives and external memory devices and their associated computer-readable media provide nonvolatile storage media for the computing device 10 on which computer-executable instructions and computer-readable data structures may be stored. Other types of media that are readable by a computer may also be used in the exemplary operation environment.

A number of program modules may be stored in the drives and RAM 20, including an operating system 38, one or more application programs 40, other program modules 42 and program data 44. In particular, application programs 40 can include programs for implementing any one of modules discussed above. Program data 44 may include any data used by the systems and methods discussed above.

Processing unit 12, also referred to as a processor, executes programs in system memory 14 and solid state memory 25 to perform the methods described above.

Input devices including a keyboard 63 and a mouse 65 are optionally connected to system bus 16 through an Input/Output interface 46 that is coupled to system bus 16. Monitor or display 48 is connected to the system bus 16 through a video adapter 50 and provides graphical images to users. Other peripheral output devices (e.g., speakers or printers) could also be included but have not been illustrated. In accordance with some embodiments, monitor 48 comprises a touch screen that both displays input and provides locations on the screen where the user is contacting the screen.

The computing device 10 may operate in a network environment utilizing connections to one or more remote computers, such as a remote computer 52. The remote computer 52 may be a server, a router, a peer device, or other common network node. Remote computer 52 may include many or all of the features and elements described in relation to computing device 10, although only a memory storage device 54 has been illustrated in FIG. 7. The network connections depicted in FIG. 7 include a local area network (LAN) 56 and a wide area network (WAN) 58. Such network environments are commonplace in the art.

The computing device 10 is connected to the LAN 56 through a network interface 60. The computing device 10 is also connected to WAN 58 and includes a modem 62 for establishing communications over the WAN 58. The modem 62, which may be internal or external, is connected to the system bus 16 via the I/O interface 46.

In a networked environment, program modules depicted relative to the computing device 10, or portions thereof, may be stored in the remote memory storage device 54. For example, application programs may be stored utilizing memory storage device 54. In addition, data associated with an application program may illustratively be stored within memory storage device 54. It will be appreciated that the network connections shown in FIG. 7 are exemplary and other means for establishing a communications link between the computers, such as a wireless interface communications link, may be used.

Although the present invention has been described with reference to preferred embodiments, workers skilled in the art will recognize that changes may be made in form and detail without departing from the spirit and scope of the invention.

What is claimed is:

1. A method of determining whether to treat soybeans for soybean aphids, the method comprising:
   collecting at least one image of a soybean canopy using one or more remote sensing instruments including a multispectral camera;
   processing the image into spectral reflectance data and selecting from the spectral reflectance data optimal spectral wavelength bands;
   classifying the selected reflectance data into one of a plurality of classification groupings using a machine learned classification model, wherein the classification groupings comprise at least a first group that corresponds with a count of aphids that is below an economic threshold count of 250 aphids per plant and a second group that corresponds with a count of aphids that is above the economic threshold count of 250 aphids per plant; and
   determining whether to treat or not treat the soybean canopy for aphids based on the classification of the reflectance data into one of the class groupings.

2. The method of claim 1, wherein selecting from the spectral reflectance data optimal spectral wavelength bands comprises selecting from the spectral reflectance data spectral wavelength bands that are indicative of soybean aphid-induced stress.

3. The method of claim 1, wherein selecting from the spectral reflectance data optimal spectral wavelength bands comprises selecting from the spectral reflectance data spectral wavelength bands that are indicative of soybean aphid-induced stress and spectral wavelength bands that eliminate false positives for soybean aphid infestation.

4. The method of claim 1, wherein the optimal spectral wavelength bands comprise red edge and near red infrared (NIR) wavelength bands.

5. The method of claim 1, wherein the machine learned classification model is trained with spectral reflectance data in the optimal spectral wavelength bands and corresponding actual aphid counts.

6. The method of claim 5, wherein the optimal spectral wavelength bands that are used to train the machine learned classification model comprise spectral wavelength bands that are indicative of soybean aphid-induced stress including at least 780 nm and 1010 nm or both.

7. The method of claim 5, wherein the optimal spectral wavelength bands that are used to train the machine learned classification model comprise spectral wavelength bands that are indicative of soybean aphid-induced stress and spectral wavelength bands that eliminate false positives for soybean aphid infestation including at least 711 nm, 789 nm, 919 nm, 1,010 nm and 1,044 nm or combinations thereof.

8. A computer system comprising:
   a camera configured to collect at least one image of a soybean canopy;
   a memory storing spectral reflectance data processed from the at least one image of the soybean canopy; and
   a processor executing instructions to perform steps comprising:
   selecting from the spectral reflectance data optimal spectral wavelength bands;
   classifying the selected reflectance data into one of a plurality of classification groupings using a machine learned classification model trained with spectral reflectance data and corresponding actual aphid counts, wherein the processor classifies the selected reflectance data into at least a first group that corresponds with a count of aphids that is below an economic threshold count of 250 aphids per plant and a second group that corresponds with a count of aphids that is above the economic threshold count of 250 aphids per plant; and determining whether to treat or not treat the soybean canopy for aphids based on the classification of the reflectance data into one of the class groupings.

9. The computer system of claim 8, wherein the optimal spectral wavelength bands comprise spectral wavelength bands that are indicative of soybean aphid-induced stress.

10. The computer system of claim 8, wherein the optimal spectral wavelength bands comprise spectral wavelength bands that are indicative of soybean aphid-induced stress and spectral wavelength bands that eliminate false positives for soybean aphid infestation.

11. The computer system of claim 8, wherein the optimal spectral wavelength bands comprise red edge and near red infrared (NIR) wavelength bands.

12. The computer system of claim 8, wherein the spectral reflectance data that the machine learned classification model is trained with comprises spectral reflectance data that is in the optimal spectral wavelength bands.

13. A method comprising:
   collecting at least one image of an area of a soybean field using a camera;
   processing the at least one image into spectral reflectance data;
   selecting from the spectral reflectance data optimal spectral wavelength bands; classifying the selected reflectance data into one of a plurality of classification groupings using a machine learned classification model trained with spectral reflective data in the select optimal spectral wavelength bands and corresponding actual aphid counts, wherein the selected reflectance data is classified into at least a first group that corresponds with a count of aphids that is below an economic threshold count of 250 aphids per plant and a second group that corresponds with a count of aphids that is above the economic threshold count of 250 aphids per plant; and
   determining whether to treat or not treat the soybean canopy for aphids based on the classification of the reflectance data into one of the class groupings.

14. The method of claim 13, wherein the optimal spectral wavelength bands comprise red edge and near red infrared (NIR) wavelength bands.

15. The method of claim 13, wherein the optimal spectral wavelength bands that are used to train the machine learned classification model comprise spectral wavelength bands that are indicative of soybean aphid-induced stress including at least 780 nm and 1010 nm or both.

16. The method of claim 13, wherein the optimal spectral wavelength bands that are used to train the machine learned classification model comprise spectral wavelength bands that are indicative of soybean aphid-induced stress and spectral wavelength bands that eliminate false positives for soybean aphid infestation including at least 711 nm, 789 nm, 919 nm, 1,010 nm and 1,044 nm or combinations thereof.

* * * * *